United States Patent [19]
Rizvi

[11] Patent Number: 6,110,186

[45] Date of Patent: Aug. 29, 2000

[54] SURGICAL FINGER PROTECTOR AND IMPLEMENT

[76] Inventor: Syed Rizvi, 6208 Castle Cary Dr., Bakersfield, Calif. 93306

[21] Appl. No.: 09/392,594

[22] Filed: Sep. 9, 1999

Related U.S. Application Data

[60] Provisional application No. 60/101,957, Sep. 23, 1998.

[51] Int. Cl.[7] .................................................. A61B 17/04
[52] U.S. Cl. ................................ 606/148; 2/21; 128/846; 128/880; 223/101
[58] Field of Search .................................. 606/101, 148; 128/846, 880; 223/101; 2/21

[56] References Cited

U.S. PATENT DOCUMENTS

| | | | |
|---|---|---|---|
| D. 124,616 | 1/1941 | Reid | 128/846 |
| 1,109,796 | 9/1914 | Sills | 294/25 |
| 1,150,724 | 8/1915 | Willsey | 223/101 |
| 3,228,033 | 1/1966 | Ames et al. | 2/21 |
| 3,511,242 | 5/1970 | Agnone | 606/148 |
| 4,308,860 | 1/1982 | Sanders et al. | 128/846 |
| 4,985,038 | 1/1991 | Lyell | 606/148 |

*Primary Examiner*—Gary Jackson
*Attorney, Agent, or Firm*—Donald A. Kettlestrings

[57] ABSTRACT

A finger protector and grasping implement for fitting over a single finger during surgical procedures includes an elongated, curved, hollow body having a cylindrical wall, a closed end wall connected to the cylindrical wall and defining an open end in opposed relationship with the closed end wall. A plurality of projections of various lengths extend outwardly from the cylindrical wall and from the end wall, and the end wall defines a groove therein to act as a safety stop for preventing undesired slipping movement of a surgical needle during surgical procedures.

17 Claims, 1 Drawing Sheet

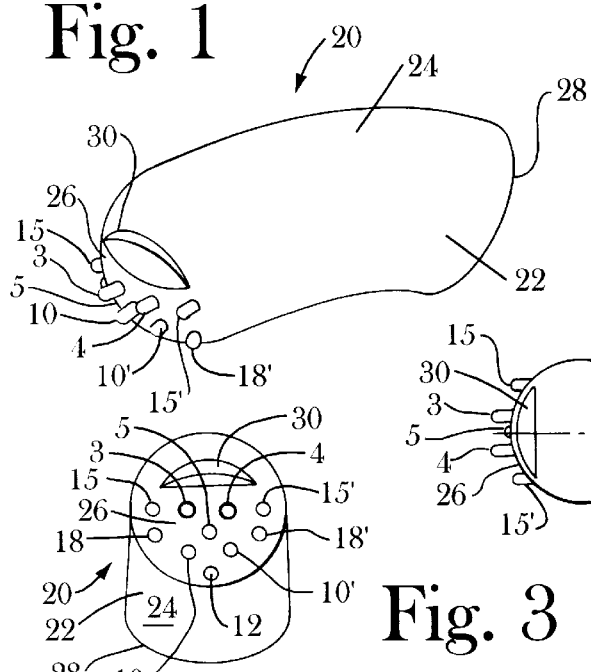
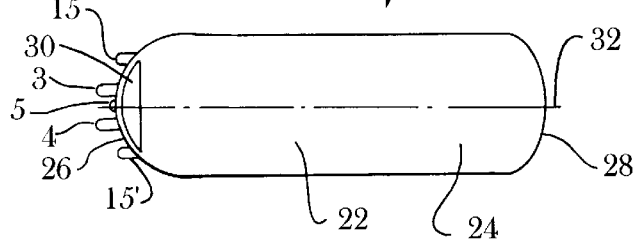
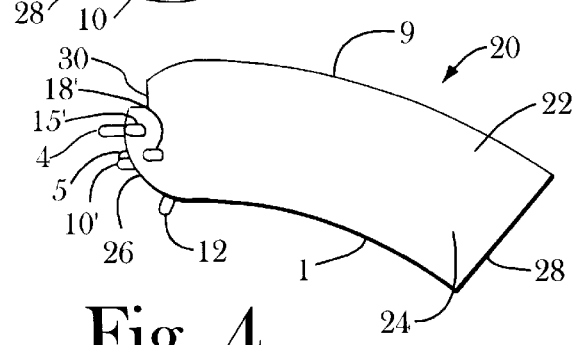
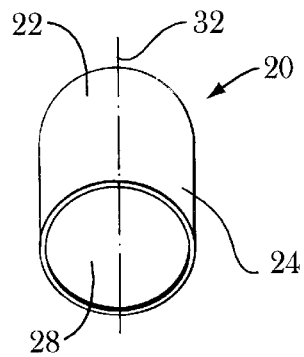
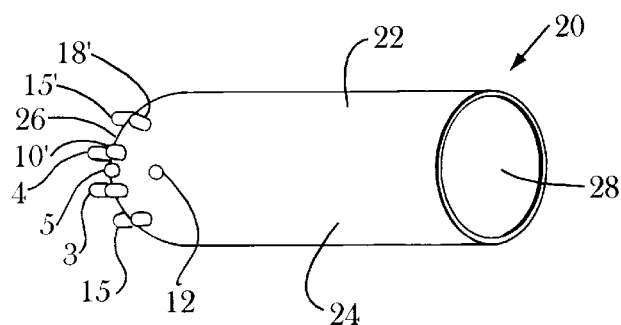

SURGICAL FINGER PROTECTOR AND IMPLEMENT

This application claims benefit of Provisional Application 60/101,957 filed Sep. 23, 1998.

BACKGROUND OF THE INVENTION

This invention relates to a finger protector and more particularly to a finger protector and grasping implement for fitting over a single finger during surgical procedures.

The use of needles in suturing during surgical procedures can place the surgeon at risk for needle stick injuries and for the possible contraction of infectious diseases, such as AIDS and hepatitis. It is important during suturing to drive the suturing needle through desired amounts of tissue to provide optimum suturing for different surgical procedures. It is also important for the surgeon to be able to view the suturing needle tip to provide the surgeon with more control during the surgical procedure, and it is important to prevent the suturing needle from slipping toward the surgeon during the surgical procedures.

It is, therefore, an object of the present invention to provide a finger protector and implement for fitting over a single finger during surgical procedures.

Another object is to provide such a protector and implement which will protect the surgeon and the patient against needle stick injuries during the surgical procedures.

A further object of the invention is the provision of such a protector and implement which will enable the surgeon to grab or grasp a specifically desired amount of tissue through which a suturing needle can be driven during the surgical procedure.

Still another object is to provide such a protector and implement which will prevent a suturing needle from slipping toward the surgeon during the surgical procedures.

Yet another object of the present invention is the provision of such a protector and implement which is configured for enabling the surgeon to view the tip of a suturing needle to provide the surgeon with more control over the suturing procedure.

A still further object is to provide such a protector and implement which is curved to comfortably fit over one finger of the surgeon and which covers approximately two-thirds of a finger inserted within the protector and implement.

Another object is to provide such a protector and implement which includes a plurality of projections of various lengths and diameters extending outwardly from the protector and implement for enabling the surgeon to grab or grasp a desired amount of tissue during a surgical procedure.

Still another object is to provide such a protector and implement which provides peace of mind for the patient and the surgeon by preventing cross-contamination and by protecting against AIDS, hepatitis and other infectious diseases.

Additional objects and advantages of the invention will be set forth in part in the description which follows, and in part will be obvious from the description, or may be learned by practice of the invention. The objects and advantages are realized and attained by means of the instrumentalities and combinations particularly pointed out in the appended claims.

SUMMARY OF THE INVENTION

To achieve these and other objects, the present invention provides a finger protector and grasping implement for fitting over a single finger during surgical procedures, comprising: an elongated, curved, hollow body having a first cylindrical wall, a closed end wall connected to the cylindrical wall, and defining an open end in opposed relationship with the closed end wall; a plurality of projections of various lengths and diameters extending outwardly from the first wall and from the end wall; and the end wall defining a groove therein to act as a safety stop for preventing undesired slipping movement of a surgical needle during a surgical procedure.

It is to be understood that both the foregoing general description and the following detailed description are exemplary and explanatory but are not restrictive of the invention.

BRIEF DESCRIPTION OF THE DRAWINGS

The accompanying drawings, which are incorporated in and constitute a part of this specification, illustrate a preferred embodiment of the invention and, together with the description, serve to explain the principles of the invention.

FIG. 1 is a perspective view of the protector and implement;

FIG. 2 is a top plan view of the protector and implement;

FIG. 3 is a front elevation view of the protector and implement;

FIG. 4 is a side elevation view of the protector and implement;

FIG. 5 is a rear end view of the protector and implement; and

FIG. 6 is a bottom plan view of the protector and implement.

DESCRIPTION OF THE PREFERRED EMBODIMENT

With reference now to the drawings, wherein like reference characters designate like or corresponding parts throughout the several views, there is shown a finger protector and implement 20 for fitting over a single finger during surgical procedures. Protector and implement 20 includes an elongated, curved, hollow body 22 having a first cylindrical wall 24, a closed end wall 26 connected to cylindrical wall 24 and defining an open end 28 in opposed relationship with closed end wall 26.

A plurality of projections 3, 4, 5, 10, 10', 12, 15, 15', 18 and 18' of various lengths and diameters extend outwardly from first wall 24 and from end wall 26. End wall 26 also defines a groove 30 therein to act as a safety stop for preventing undesired slipping movement of a surgical needle (not shown) during a surgical procedure.

In accordance with the invention, the plurality of projections 3, 4, 5, 10, 10', 12, 15, 15', 18 and 18' include a first plurality of said projections 3, 4 defining a first predetermined length and diameter, and a second plurality of said projections 5, 10, 10', 12, 15, 15', 18 and 18' defining lengths and diameters different than the first predetermined length and diameter of projections 3, 4.

Protector and implement 20 is symmetrical about an imaginary center-line plane 32, shown in FIGS. 2 and 5.

Each of projections 3, 4, 5, 10, 10', 12, 15, 15', 18 and 18' is preferably cylindrical in shape, and each of projections 5, 10, 10', 12, 15, 15', 18 and 18' defines a substantially identical diameter dimension. Projections 3, 4 preferably define equal diameters greater than the diameters of the remaining projections. Each of projections 3, 4, 5, 10, 10', 12, 15, 15', 18 and 18' also preferably defines a hemispherical distal end. Protector and implement 20 is preferably of sufficient length to cover substantially two-thirds of an index finger inserted therein.

In accordance with the invention, first plurality of projections 3, 4 are two in number and are located immediately adjacent to groove 30. The second plurality of said projections 5, 10, 10', 12, 15, 15', 18 and 18' includes third projection 5 located on center-line plane 32 and adjacent to first plurality of projections 3, 4 for stopping slippage of a surgical needle (not shown) toward the surgeon and for enabling the surgeon to view the tip of the surgical needle during a surgical procedure.

The second plurality of projections 5, 10, 10', 12, 15, 15', 18 and 18' further includes a fourth projection 12 located on center-line plane 32 and adjacent to third single projection 5. Projection 12 also acts to stop slippage of a surgical needle toward the surgeon during a surgical procedure.

The second plurality of projections 5, 10, 10', 12, 15, 15', 18 and 18' further includes a plurality of fifth projections 10, 10' located immediately adjacent to third projection 5. The second plurality of projections 5, 10, 10', 12, 15, 15', 18 and 18' also includes a plurality of sixth projections 18, 18', respectively located adjacent to fifth projections 10, 10'.

Further in accordance with the invention, the second plurality of projections 5, 10, 10', 12, 15, 15', 18 and 18' also includes a plurality of seventh projections 15, 15' located adjacent to first projections 3, 4.

The first and second plurality of projections 3, 4, 5, 10, 10', 12, 15, 15', 18 and 18' are preferably from 0.060 to 0.151 inch in length and projections 5, 10, 10', 12, 15, 15', 18 and 18' are each preferably 0.062 inch in diameter. Projections 3, 4 are each preferably 0.090 inch in diameter. The following table shows the preferred lengths of each of projections 3, 4, 5, 10, 10', 12, 15, 15', 18 and 18'.

| Projections | Length |
|---|---|
| 3 | .149 |
| 4 | .149 |
| 5 | .060 |
| 10, 10' | .104 |
| 12 | .151 |
| 15, 15' | .083 |
| 18, 18' | .109 |

It should be understood that the lengths of the projections shown in the the above-referenced table may vary by a factor of plus or minus one or two millimeters. Projections of greater lengths than those discussed herein would make protector and implement 20 too large to comfortably handle and would not improve the practical benefits of the projections. Projections of smaller lengths than those discussed herein would compromise the benefits of the projections, as discussed herein.

In operation and use, protector and implement 20 is positioned onto a finger of the surgeon by inserting the finger through open end 28. Although protector and implement 20 can be used on any finger, it is preferred that it be positioned on the index finger of the surgeon. A plurality of protectors and implements 20 can also be positioned onto a plurality of fingers.

The curved configuration of hollow body 22 allows a finger to comfortably fit within protector and implement 20, and the curved configuration allows for better grasping from inside protector and implement 20 by bending of the finger. The curved configuration of body 22 also enhances comfort for the surgeon and allows for easier use of protector and implement 20 because the surgeon's fingers are typically slightly bent during surgical procedures.

The length of protector and implement 20 is such that it preferably covers approximately two-thirds of the length of a finger inserted therein to provide protection against needle stick injuries.

A plurality of projections 3, 4, 5, 10, 10', 12, 15, 15', 18 and 18' of various lengths and diameters permits the surgeon to grab as much or as little tissue as he wants during the surgical procedure, depending upon the type of operation or the surgeon's preference. To grab and suture more tissue, the surgeon drives a needle (not shown) between longer projections. To grab and suture less tissue, the surgeon drives a needle between projections of shorter lengths. Projections 5 and 12 not only permit the surgeon to drive the needle through a desired amount of tissue, but they also prevent undesired slipping movement of a needle during a surgical procedure. Projection 5 is specifically designed to stop the needle from slipping towards the surgeon as well as to provide a view of the needle tip during the surgical procedure. The shorter length of projection 5 prevents projection 5 from obscuring the surgeon's view of the needle tip during the surgical procedure.

Groove 30 also acts to prevent undesired slipping movement of a surgical needle during a surgical procedure. If the needle slips and moves toward the back of protector and implement 20, the needle will fall into groove 30 to provide an extra safety feature for the surgeon and the patient.

Protector and implement 20 provides safety not only with needles but also with other sharp surgical instruments. Protector and implement 20 can be used in any surgical procedure, and protector and implement 20 is preferably made out of strong plastic material or polycarbonate so that protector and implement 20 is disposable. Disposability is an important feature for preventing cross-contamination and protects against transmittal of AIDS, hepatitis and other infectious diseases. Protector and implement 20 can also be made from stainless steel.

When tissue is grabbed by the surgeon using protector and implement 20, projections 3, 4, 5, 10, 10', 12, 15, 15', 18 and 18' of different lengths allow the surgeon to drive the needle between the projections and to grab and suture the desired amount of tissue. The longer the length of the projection used to grab tissue, the more tissue is grabbed and sutured. The surgeon can also drive a needle over and not in between the smaller projections if the surgeon does not want to penetrate tissue all the way through and wants to keep the suture just above a predetermined tissue.

The invention in its broader aspects is not limited to the specific details shown and described, and departures may be made from such details without departing from the principles of the invention and without sacrificing its chief advantages.

What is claimed is:

1. A finger protector and implement for fitting over a single finger during surgical procedures, comprising:

an elongated, curved, hollow body having a first substantially cylindrical wall, a closed end wall connected to said cylindrical wall, and defining an open end in opposed relationship with said closed end wall;

a plurality of projections of various lengths extending outwardly from said first wall and from said end wall; and said end wall defining a groove therein to act as a safety stop for preventing undesired slipping movement of a surgical needle during a surgical procedure.

2. A protector and implement as in claim 1 wherein said projections include:
   a first plurality of said projections defining a first predetermined length; and
   a second plurality of said projections defining lengths different than said first predetermined length.

3. A protector and implement as in claim 2 wherein said protector and implement is symmetrical about an imaginary center-line plane.

4. A protector and implement as in claim 3 wherein each of said projections is substantially cylindrical in shape.

5. A protector and implement as in claim 4 wherein each of said projections defines a substantially hemispherical distal end.

6. A protector and implement as in claim 5 which covers substantially two-thirds of a finger inserted therein.

7. A protector and implement as in claim 6 wherein said first plurality of projections are two in number and are located immediately adjacent to said groove.

8. A protector and implement as in claim 7 wherein said second plurality of projections includes a third projection located on said center-line plane and adjacent to said first plurality of projections for stopping slippage of a surgical needle toward the surgeon and for enabling the surgeon to view the tip of a surgical needle during the surgical procedure.

9. A protector and implement as in claim 8 wherein said second plurality of projections further include a fourth projection located on said center-line plane and adjacent to said third projection.

10. A protector and implement as in claim 9 wherein said second plurality of projections further include a plurality of fifth projections located adjacent to said third projection.

11. A protector and implement as in claim 10 wherein said second plurality of projections further include a plurality of sixth projections located adjacent to said fifth projections.

12. A protector and implement as in claim 11 wherein said second plurality of projections further include a plurality of seventh projections respectively located adjacent to said first projections.

13. A protector and implement as in claim 12 wherein said first and second plurality of projections are substantially from 0.060 to 0.151 inch in length, wherein said first plurality of projections are each substantially 0.090 inch in diameter and wherein said second plurality of projections are each substantially 0.062 inch in diameter.

14. A protector and implement as in claim 12 wherein said first plurality of projections are each substantially 0.149 inch in length.

15. A protector and implement as in claim 14 wherein said third projection is substantially 0.060 inch in length.

16. A protector and implement as in claim 15 wherein said fourth projection is substantially 0.151 inch in length; said fifth projections are substantially 0.104 inch in length; said sixth projections are substantially 0.109 inch in length; and said seventh projections are substantially 0.083 inch in length.

17. A protector and implement as in claim 3 wherein said second plurality of said projections include third and fourth projections located on said center-line plane for preventing undesired slipping movement of a surgical needle during a surgical procedure and for enabling a surgeon to view a needle tip during a surgical procedure.

* * * * *